United States Patent [19]

Halpern

[11] Patent Number: 5,468,243
[45] Date of Patent: Nov. 21, 1995

[54] FEMORAL SUPERIOR NECK REMODELLING MEANS AND METHOD

[76] Inventor: Alan A. Halpern, 1400 Low Rd., Kalamazoo, Mich. 49008

[21] Appl. No.: 143,858

[22] Filed: Oct. 27, 1993

[51] Int. Cl.⁶ ............................ A61B 17/16; A61B 17/17
[52] U.S. Cl. ................................ 606/80; 606/89; 409/179
[58] Field of Search ................................ 606/89, 80, 86, 606/96, 87, 79; 409/178, 179

[56] References Cited

U.S. PATENT DOCUMENTS

| 4,777,942 | 10/1988 | Frey et al. | 606/80 |
| 5,133,766 | 7/1992 | Halpern | 606/89 |
| 5,147,364 | 9/1992 | Comparetto | 606/87 |
| 5,228,459 | 7/1993 | Caspari et al. | 606/96 |

Primary Examiner—Tamara L. Graysay
Attorney, Agent, or Firm—Gordon W. Hueschen

[57] ABSTRACT

A reaming device for use in creating a cavity or excavation in a femoral neck which is adapted to receive an intramedullary insert, and especially an upper flange or offset of an intramedullary insert, is disclosed, as well as a method for producing such a cavity or excavation in the femoral neck, preferably in a flattened and elongated superior neck of a previously-resected femoral head. The apparatus provides a camming surface in contact with a corresponding cam follower for longitudinal manipulation of the rotatory reamer into and within the upper portion of the femoral head to create the desired cavity or excavation therein as the rotary reamer is moved back and forth generally laterally.

19 Claims, 3 Drawing Sheets

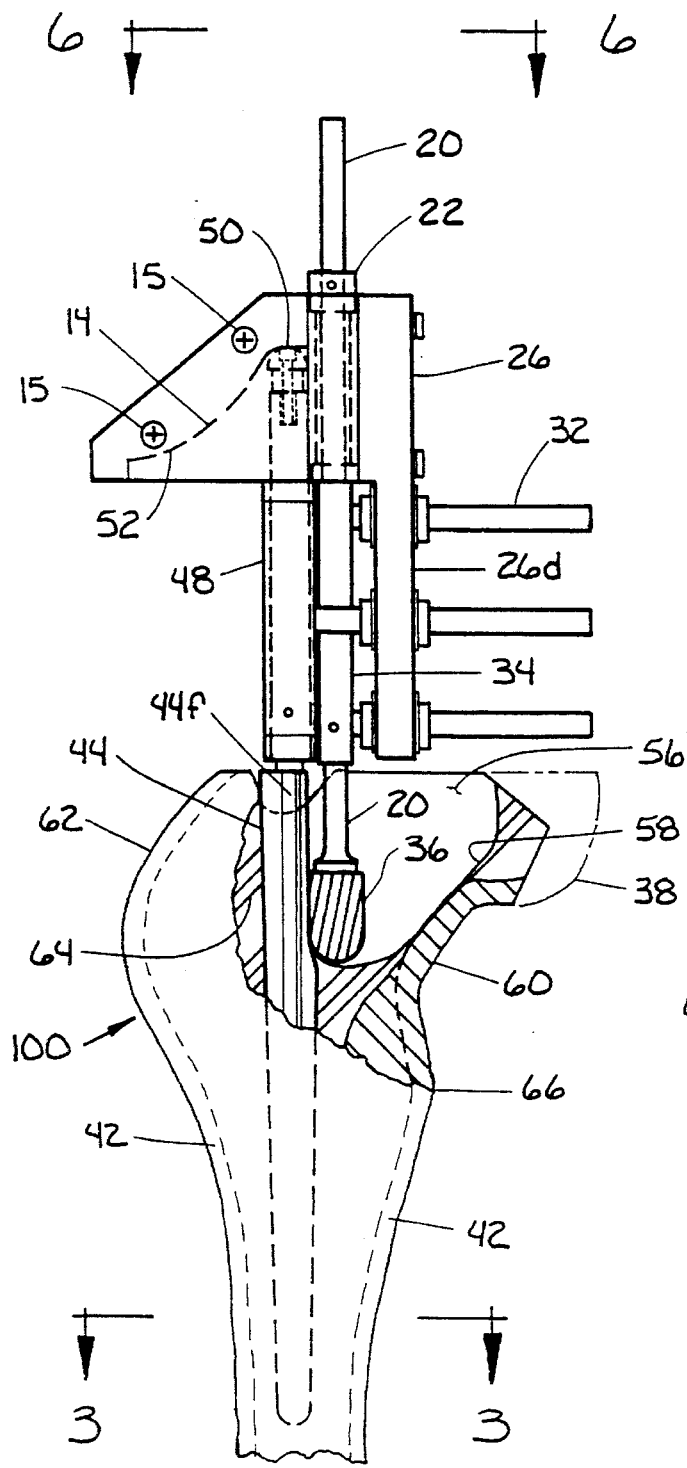
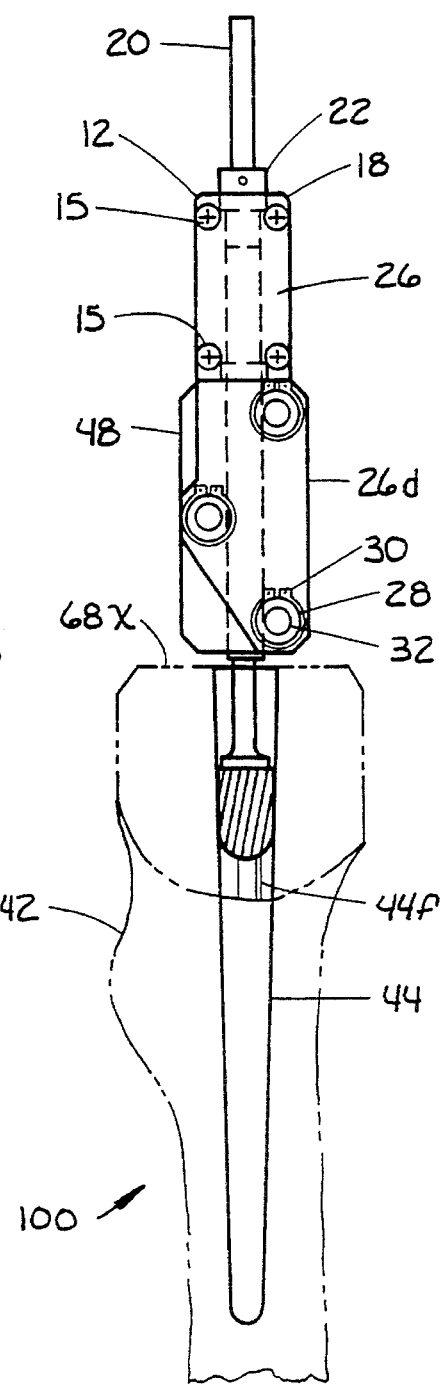
Fig. 4
Fig. 5

FEMORAL SUPERIOR NECK REMODELLING MEANS AND METHOD

BACKGROUND OF THE INVENTION

1. Field of the Invention

The present invention relates to a novel reamer means for use in remodeling a femoral superior neck to provide an excavation in the cortico-cancellous bony envelope thereof for facilitating acceptance therein of a prosthetic means in the form of an intramedullary insert, especially an intramedullary insert having an upper offset or flange, and a method for such remodeling or excavating.

2. Prior Art

The prior art in this field is well set forth in my prior U.S. Pat. No. 5,133,766 which, among other things, discloses a novel femoral insert and a drilling fixture or jig for use in connection with the remodeling of a femoral head to facilitate insertion thereinto of an intramedullary insert which normally, in its finished form, includes an attached or integral shell or cap, so that the remodeled femoral head including the intramedullary insert may be employed with an intact acetabulum, namely, the cup-shaped socket in the hip bone, or in combination with a prosthetic acetabular socket or cup of a type widely available from orthopedic supply organizations today.

In my prior patent, the drilling fixture or jig was particularly adapted to produce a cavity in the femoral head which corresponded to the particular shape or configuration of the offset portion of the intramedullary insert disclosed in my said earlier patent, which was provided with a wedge-shaped offset comprising a plurality of adjoining convexly-arcuate surface segments. In the present case, the reamer device or means of the present invention is particularly adapted for the creation of a suitable excavation or cavity in the femoral superior neck for the reception therein of an intramedullary insert, and especially an upper flange or offset portion of an intramedullary insert, which offset portion may take various shapes, forms, and sizes, but especially an intramedullary insert which has an offset portion having not necessarily parallel but essentially planar sides, which offset is readily insertable into the cavity thus produced, and which optimally conforms precisely to the shape, form, and size, including the width and length and depth of the cavity, but which may if desired by the surgeon be additionally secured therein by the employment of the usual surgical hammer, cement, or the like. When the offset portion of the intramedullary insert does not have planar sides corresponding to the cavity or excavation produced using the reamer means of the present invention, but which optionally may have concave or convex side surfaces, or side surfaces comprising apertures or indentations, the cavity produced by employment of the reamer means of the present invention is equally suitable for the reception of such offset portion of an intramedullary insert. In such case it generally becomes more essential that the offset portion of the intramedullary insert be further secured in the cavity by the employment of the usual medical hammer, cement or the like, although it is possible even in such cases that the close fit between the offset portion of the intramedullary insert and the cavity produced using the reamer means and method of the present invention is sufficiently corresponding and close or tight so that no excessively forceful hammering or medical cement may be required, all of course as determined by the orthopedic surgeon in charge.

Although the intramedullary insert of my prior patent and the drilling fixture or jig disclosed therein are highly advantageous, not all intramedullary inserts have or will have the type of offset portion disclosed and claimed in my prior patent, and many will comprise an offset portion having essentially planar side surfaces, with or without apertures, porous coatings, grooves, pits, or indentations, so that an improved reamer means which is particularly adapted for the creation of a cavity in the femoral superior neck which will be adaptable to and even especially suitable for the reception therein of such type of intramedullary insert, as well as intramedullary inserts which do not comprise an offset portion having essentially planar side surfaces, has now become a requirement, want, or need of the art, and the present invention is designed to fulfill such need for a reamer device or means, which is generally applicable and widely adaptable to numerous types of intramedullary inserts with numerous types of offset portions including even an insert according to my prior invention and patent, as well as a method for producing a cavity in the femoral head therewith, in a convenient and reliable manner.

OBJECTS OF THE INVENTION

It is an object of the present invention to provide a novel reamer means for use in the remodeling of a femoral head to provide an excavation or cavity therein, and a method of providing such an excavation or cavity in the femoral superior neck which is adapted to receive a variety of femoral or intramedullary inserts having a variety of upper offsets or flanges and which may be conveniently and reliably employed when utilizing the reamer means or device of the present invention. A further object is to provide a device which can be employed to prepare the femoral bone to correspond precisely to the shape of the implant to be employed so that bony ingrowth is more likely to occur throughout the implant and so that, with more successful bony ingrowth, force transmission is more likely to be physiologic, leading to greater longevity and more predictable relief of pain. Additional objects will become apparent as the description proceeds and still other objects will be readily apparent to one skilled in the art.

In the directional designations as used herein in the specification, claims, and Abstract Of The Disclosure, the term "longitudinal" and its various modifications refers to a direction coincident with or generally parallel to the longitudinal axis of the positioning shaft 44. The term "lateral" and its various modifications refers to a direction transverse to or non-parallel with the longitudinal axis of the positioning shaft 44. The term "proximal" refers to the direction of the end of the positioning shaft 44 designed to remain external of the intramedullary canal of the femur. The term "distal" refers to the direction of the end of the positioning shaft which is designed to be inserted into the intramedullary canal of the femur.

SUMMARY OF THE INVENTION

What I believe and claim to be my invention, then, comprises the following, inter alia, singly or in combination:

A rotary reamer device adapted for use in providing an excavation in a femoral superior neck, comprising the following elements in combination:

positioning means adapted to position said rotary reamer device with respect to said femoral neck, cam follower means associated with said positioning means, rotary reamer means mounted for rotation and adapted for longitudinal and lateral movement and comprising associated longitudinal-varied camming surface means in moveable contact relationship with said cam follower means, whereby generally lateral movement of said rotary reamer means causes said cam follower means to travel along said camming surface means and said rotary reamer means to seek a longitudinal elevation corresponding to said camming surface means and thereby create in said femoral head a cavity corresponding in depth to said camming surface means;

such a device adapted for use in providing an excavation in a femoral superior neck, comprising the following elements in combination:

positioning means adapted to position said rotary reamer device with respect to said femoral neck, longitudinal cam follower means associated with said positioning means, mounting means adapted for longitudinal and lateral movement, rotary reamer means mounted for rotation in said mounting means and moveable together therewith, said mounting means comprising associated longitudinal-varied camming surface means in moveable contact with said longitudinal cam follower means, whereby generally lateral movement of said mounting means and said rotary reamer means mounted therein causes said longitudinal cam follower means to travel along said camming surface means and said rotary reamer means to seek a longitudinal elevation corresponding to said camming surface means and thereby create in said femoral head a cavity corresponding in depth to said camming surface means;

such a device, wherein said positioning means comprises shaft means adapted to be inserted in the intramedullary canal of a femur;

such a device, wherein said positioning means comprises an essentially longitudinal member which is capped by said cam follower means; such a device, wherein said essentially longitudinal member is in slidable relationship with longitudinally moveable sleeve means which is connected to said mounting means and movable longitudinally together therewith;

such a device, wherein said mounting means comprises a lower extension which is apertured for slidable movement therein of essentially lateral rod means extending from said sleeve means and adapted for essentially lateral movement from a distal position to a proximal position with respect to said sleeve means and vice versa;

such a device, wherein said shaft means is flanged or fluted to prevent rotation and is radiused at a proximal end to permit close juxtaposition thereof with said reamer means;

such a device, wherein said rotary reamer means is adapted to be rotatively driven from a rotative power-supply source;

and such a device, wherein said rotary reamer means is mounted on shaft means which is adapted to be rotatively driven from a rotative power-supply source.

Moreover a method for providing an excavation in a femoral superior neck comprising the steps of 1) providing rotary reamer means mounted for longitudinal and lateral movement and associated longitudinally-varied camming surface means and 2) providing positioning means for positioning said rotary reamer means with respect to said femoral neck including associated cam follower means movably in contact relationship with said camming surface means, so that generally lateral movement of said rotary reamer means causes said cam follower means to travel along said camming surface means and said rotary reamer means to seek a longitudinal elevation corresponding to said camming surface means and thereby create a cavity in said femoral head corresponding in depth to said camming surface means, and 3) moving said rotary reamer means back and forth generally laterally until completion of said excavation;

such a method for providing an excavation in a femoral superior neck comprising the steps of 1) providing mounting means which is mounted for longitudinal and lateral movement and rotary reamer means mounted therein for movement together therewith, said mounting means comprising associated longitudinally-varied camming surface means and 2) providing positioning means including longitudinal cam follower means movingly in contact with said camming surface means, so that generally lateral movement of said mounting means causes said cam follower means to travel along said camming surface means and said rotary reamer means to seek a longitudinal elevation corresponding to said camming surface means and thereby create a cavity in said femoral head corresponding in depth to said camming surface means, and 3) moving said mounting means and reamer means mounted therein back and forth generally laterally until completion of said excavation;

such a method, wherein said positioning means comprises shaft means adapted to be inserted in the intramedullary canal of a femur and including the step of so inserting said shaft means;

such a method, wherein said positioning means comprises an essentially longitudinal member which is capped by said cam follower means and including the step of moving said cam follower means along said camming surface means;

such a method, wherein said essentially longitudinal member is in slidable relationship with longitudinally moveable sleeve means which is connected to said mounting means and movable longitudinally together therewith and including the step of moving said sleeve means longitudinally with respect to said longitudinal member;

such a method, wherein said mounting means comprises a lower extension which is apertured for slidable movement therein of essentially, lateral rod means extending from said sleeve means and adapted for essentially lateral movement from a distal position to a proximal position with respect to said sleeve means and vice versa and including the steps of moving said lower extension toward and away from said sleeve means;

such a method, wherein said shaft means is flanged or fluted to prevent rotation and is radiused at an upper end to permit close juxtaposition thereof with said reamer means and including the step of employing said shaft means;

such a method, wherein said rotary reamer means is adapted to be rotatively driven from a rotative power-supply source and including the step of so driving said rotary reamer means;

and such a method, wherein said rotary reamer means is mounted on shaft means which is adapted to be rotatively driven from a rotative power-supply source and including the step of so driving said shaft means.

Finally, a method for excavating the upper end of a femur to provide an excavation therein suitable for the acceptance of an intramedullary insert and an upper flange or offset thereof, which comprises the step of utilizing any such device as described in the foregoing.

BRIEF DESCRIPTION OF THE DRAWINGS

FIG. 4 is the same as FIG. 2, but shows the reamer means of the invention in a retracted closed or downwardmost position.

FIG. 5 is a right-hand view of FIG. 4, the outline of the femur again being shown in shadow lines.

DETAILED DESCRIPTION OF THE INVENTION

In usual methodology for total or partial hip joint replacement, following dislocation of the hip joint, virtually the entire superior neck of the femur is frequently removed although, in the approach of my previous patent and other advanced practices, only the minimum amount of bone is removed from the surface of the head of the femur to expose healthy, firm bone surfaces, whereafter the prosthetic femoral insert is placed into position and secured in such position to provide a replacement hip joint surface, ordinarily of metal, having the configuration of a ball (i.e., the femoral head) of substantially the same size, or standard replacement diameters of 22 mm, 26 mm, 28 mm, or 32 mm, in substantially the same location and with the same center of rotation as the original ball, whereafter the replaced femoral head and the acetabulum or acetabulum socket member are relocated in rotatable engagement with one another. The amount of bone removed from the femoral head depends upon the practice of the orthopedic surgeon in charge and the type of insert to be employed, but some bone is generally eliminated as representatively depicted in the FIGS.

Figure 1:
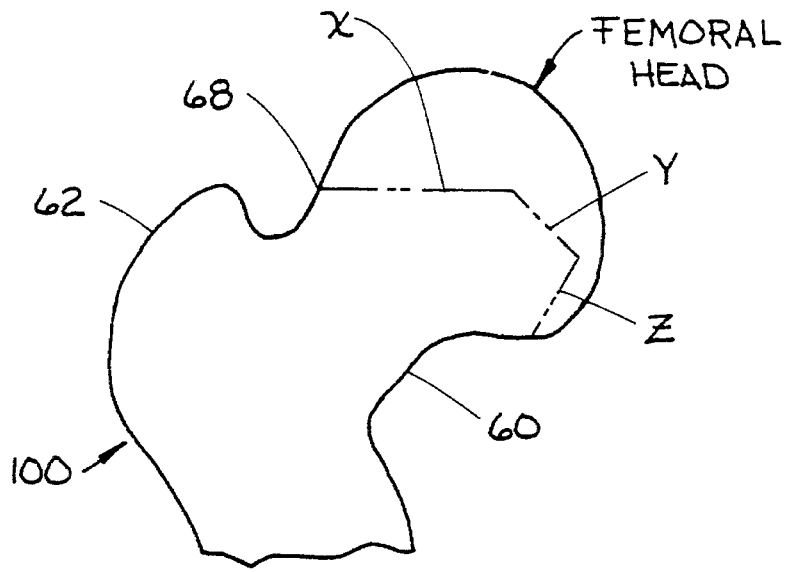
FIG. 1 is a side view of the upper portion of a femur, including the femoral head, superior neck, calcar or inferior neck, and greater trochanter, illustrating in phantom lines the manner in which the femoral head may be resected in accord with usual remodeling practice to expose the superior neck of the femur or femoral head.
Figure 2:
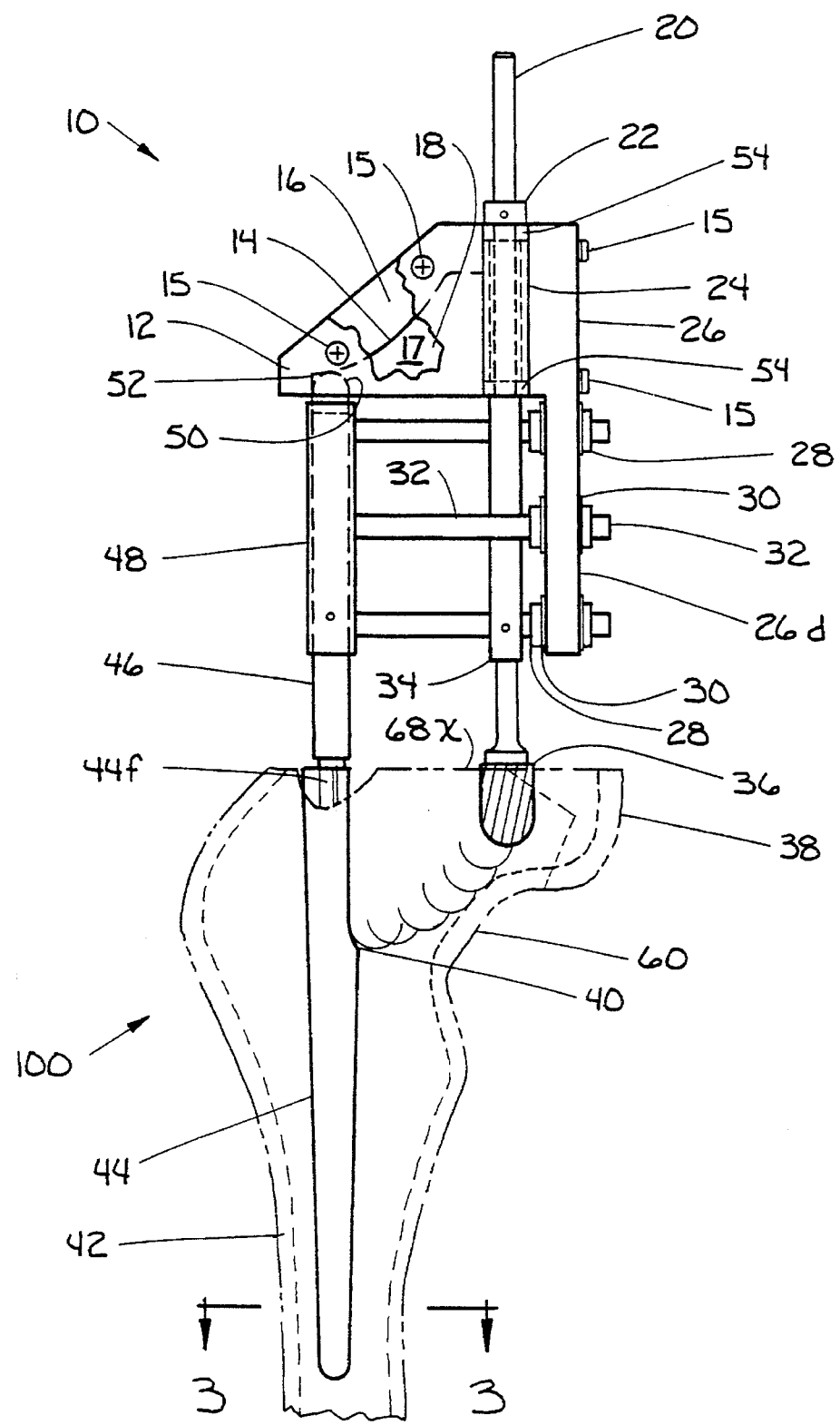
FIG. 2 is a partially cut-away side view of the reamer means of the invention in its extends, opened up or upwardmost position mounted upon a positioning shaft essentially longitudinally disposed in the intramedullary canal of the femur, the outline of the femur being shown in shadow lines.

Referring now more particularly to the drawings for a better understanding of the invention, wherein the same numbers are used to refer to the same elements or members throughout:

FIG. 1 shows the upper portion of a femur 100 before resection of the femoral head, including the superior neck 68, the calcar or inferior neck 60, and the greater trochanter 62, with cuts for preferred resection of the femoral head for use in conjunction with the reamer means 10 of the present invention being indicated by the shadow lines X, Y, and Z. Of course, in accord with the method or procedure utilized, the first step can well be and usually is a resection of the femoral head although, as will be apparent to one skilled in the art from the following description of the method of the invention and the reamer means 10 also provided according to the invention, it is not always necessary that the femoral head be fully resected prior to reaming of the same and, in some cases, as will also be apparent to one skilled in the art, the reaming operation may be effected advantageously prior to resection or a complete resection. However, resection at least along the phantom line X, to produce an extended and flattened superior neck 68 at 68X, is generally and advantageously carried out prior to the reaming operation to provide a closer fit with reaming means 10, as shown in FIGS. 2, 4, and 5. Resection along phantom lines Y and Z at this stage is optional and varies from case to case with the surgeon in charge of the particular operation, it ordinarily not being necessary to effect resection along the other two lines Y and Z as shown in FIG. 1 prior to the reaming operation. In practice, however, resection of the femoral head prior to the reaming operation preferably comprises resection of the upper surface of the femoral head to produce a resected superior neck surface 68X as shown in FIGS. 2, 4, and 5, thereby producing an upper substantially planar surface in the resected femoral superior neck for purposes of corresponding to an upper substantially planar surface of a femoral insert which will in place generally lie in the same plane as or somewhat above or below the planar essentially lateral surface of the resected femoral superior neck, now having an extended and flattened superior neck 68X, again as shown in FIGS. 2, 4, and 5. The other cuts Y and Z shown in FIG. 1 are sometimes advantageously also made prior to the reaming operation but may, as already described, be postponed until after the reaming operation is completed, depending somewhat inter alia upon the condition of the bone. In some cases the resection will be along an extended line Y and resection along the line Z will be omitted.

Now, proceeding to FIG. 2, the upper portion of the femur including the greater trochanter, the lesser trochanter, the extended superior neck 68X, and the calcar or inferior neck 60, are all visible in shadow lines, along with a portion of the femur identified as 38 which may be removed after the resection if not before, as desired by the surgeon in charge of the operation.

Figure 3:
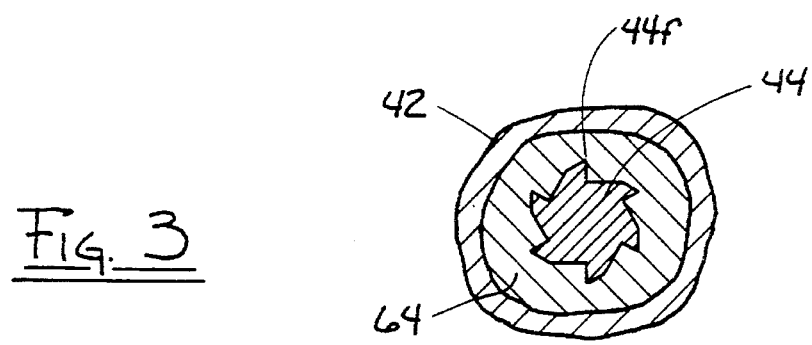
FIG. 3 is a cross-sectional view of a femur, taken along line 3—3 of FIGS. 2 and 4, below the lesser trochanter, showing the positioning shaft geometry whereby the positioning shaft is prevented by flanges or flutes from rotation while in place within the intramedullary canal.

From FIG. 2 can be seen the reamer means or device 10 of the present invention in its extended open or upwardmost position, with the positioning shaft 44 thereof with its ridges, flanges, or flutes 44f securely locking the positioning shaft 44 within the central channel of the intramedullary canal of the femur after removal of cancellous bone therefrom. The cross-sectional view of FIG. 3 taken below the lesser trochanter as indicated in FIGS. 2 and 4 shows the positioning shaft 44 with its flutes 44f securely locked within the intramedullary canal in the softer or cancellous bone 64, in turn contained within the outer and harder femoral cortex 42.

Returning to FIG. 2, the reamer means of the invention 10 is shown mounted atop the femur 100. Securely mounted to the top of positioning shaft 44, which may be radiused at 40 if necessary or desirable to provide room for reamer 36 when in close juxtaposition thereto, is longitudinal guide shaft 46, usually cylindrical, upon which lateral guide rod 32 holder in the form of extendibly and retractably-moveable sleeve or sleeveblock 48 is mounted in sliding engagement therewith. At the proximal end of guide shaft 46 is mounted cam dog or cam follower 50, as shown in contact with longitudinally-varied camming surface 52 of inwardly disposed edge 14 provided by middle guide plate 16 and to be followed by cam follower or cam dog 50 during the course of excavating with the device of the invention. Upper guide block 26 comprises bearings or sleeves 28 retained in a downwardly disposed longitudinal leg 26d thereof by means of retaining rings 30, as well as a spacer block 24 comprising a longitudinal through-hole for the mounting therein of top and bottom bearings 54 in which longitudinal shaft 20 is mounted for rotation, and also comprises front and rear cover plates 12 and 18, leaving an open area 17 therebetween which is bounded by the adjacent longitudinal side of spacer block 24 and the innermost edge 14 of middle guide plate 16. This inwardly-disposed curved edge 14 provides an inwardly-disposed surface 52 which acts as a camming surface to be followed by cam dog or cam follower 50 atop longitudinal guide shaft 46 to provide a proper cutting path for the reamer 36 which is releasably and preferably interchangeably or otherwise secured to a lower extension 34 of longitudinal shaft 20. As shown in FIG. 2, cam follower or dog 50 rests against camming surface 52 at its lowest point, which means that reamer 36, as supported on shaft 20 by block 26, is in turn supported by its laterally-moveable undercarriage assembly including downward extension 26d and cylindrical bearings or sleeves 28 and retaining rings 30 on lateral rods 32, which in turn are secured to sliding sleeve 48 for longitudinal movement therewith. Longitudinal shaft 20 is mounted for rotation in bearings 54 in spacer block 24 and is retained in proper position with respect to spacer block 24 by means of locking collar 22. The rotary reamer 36 as shown is in essentially cylindrical form with a rounded bottom but may take any one of a wide variety of sizes, shapes and forms, e.g., cylindrical with pointed end, pyramidal, conical, or the like, most of which are entirely conventional, the exact size, shape, and form of the reamer being selected by the surgeon depending upon the size and configuration of the cavity to be provided in the particular femoral head being excavated.

Three lateral rods 32 are shown integral with or secured as by welding, brazing, or the like, to longitudinally-sliding sleeve 48 and extend laterally on both sides of longitudinal shaft 20 extension 34, being slidingly mounted in cylindrical bearings or sleeves 28, in turn retained in longitudinal and distal extension 26d of guide block 26 by means of retaining rings 30. The rotary reamer 36 is shown partially extending into the upper surface of the extended and flattened superior neck 68X and the proximal end of longitudinal shaft 20 is adapted to be connected to a rotatory power-supply source for rotation of longitudinal shaft 20 including lower extension 34 thereof which as shown is releasably secured to reamer 36. As shown in FIG. 2, sleeve 48 is shown in an extended longitudinal with respect to the distal end of guide shaft 46 with which it is in longitudinal sliding relationship, and can be lifted further longitudinally at the commencement of reaming operations so as to place reamer 36 initially at surface 68X. Cam dog or follower 50 is shown in contact with the distalmost portion of camming surface 52 of innermost edge 14 of middle guide plate 16 so that guide block 26 positions reamer 36 mounted for rotation therein at a position relatively near the surface 68X of the superior neck of resected femur 100, where it will remain until cam dog 50 traverses the reach of camming surface 52 provided at innermost longitudinally-varied edge 14 of middle guide plate 16, which in turn brings sleeve 48 and reamer 36 into a distal position. Thus, by movement of guide block 26 and its distal extension 26d from right to left upon rods 32 the entire guide block 26 and its distal extension 26d, together with the elements carried thereby, are lowered to their distal position, in close juxtaposition to sleeve 48, and reamer 36 is correspondingly lowered into the inner layer of softer or cancellous bone 64 interior of the femoral cortex 42, thus providing a constantly-deepening excavation or cavity 56 in the superior neck of the femur, i.e., in the resected femoral head, which is of suitable depth and configuration for the insertion of an proximal flange or offset portion of an intramedullary femoral insert to be inserted thereinto, until reamer 36 comes into close juxtaposition with positioning shaft 44 at radiused portion 40 thereof, all as shown in FIG. 4.

As seen in FIG. 4, movement of guide block 26 and its distal extension 26d laterally toward the axis of the positioning shaft 44 along rod means 32 has brought cam dog or cam follower 50 into contact with the uppermost reach of camming surface 52 at the innermost edge 14 of middle guide plate 16 and has correspondingly brought extension 34 of shaft 20 into juxtaposition with sleeve 48 and has as a result correspondingly forced reamer 36 into its lowermost position at the bottom of cavity or excavation 56 and incidentally also into close juxtaposition with radiused portion 40 of positioning shaft 44, which radiused portion 40 may in fact be provided specifically to permit just such precise or snug juxtaposition.

In the right-hand view of FIG. 4 as shown in FIG. 5, the elongated and flattened surface of the superior neck 68X of the resected femoral head is apparent as are all of the other previously-described elements or members, and in particular cylindrical bearings or sleeves 28, retaining rings 30, and the ends of rods 32 retained therein, as well as screws 15 which secure the boxlike structure of guide and support block 26 together at its distal and proximal upper ends.

Figure 6:
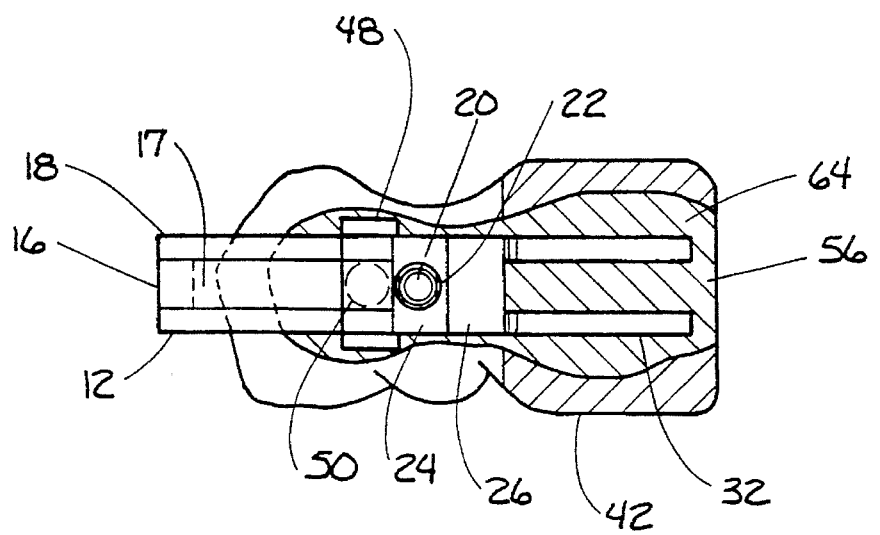
FIG. 6 is a top plan view of FIG. 4.

From the top view of FIG. 6, which corresponds to the side view of FIG. 4, various of the already-described elements or members are visible, as well as the excavation or cavity 56 from the softer or cancellous bone 64 surrounded by the femoral cortex 42. The guide and support block 26 lower extension 26d is in close juxtaposition to sleeve 48, just as in FIG. 4, and block 26 overlaps the same in this view, again just as in FIG. 4.

According to the method of the invention, in operation the method of the invention is essentially providing rotary reamer means mounted for longitudinal and lateral movement and associated longitudinally-varied camming surface means and providing positioning means for positioning said rotary reamer means with respect to said femoral superior neck including associated cam follower means movably in contact relationship with said camming surface means, so that generally lateral movement of said rotary reamer means causes said cam follower means to travel along said camming surface means and said rotary reamer means to seek a longitudinal position corresponding to said camming surface means and thereby create a cavity in said femoral head corresponding in depth to said camming surface means, and moving said rotary reamer means back and forth generally laterally until completion of said excavation, all with appropriate activation of the rotary power-supply source, as will be apparent from the foregoing, and especially from the foregoing description of the reamer device, means, or apparatus of the invention and the accompanying explanation of how it operates.

In conclusion, from the foregoing, it is apparent that the present invention provides a novel reamer means for the reconstruction of a femoral shaft and neck so as to provide an excavation or aperture therein for the reception of the offset portion of a suitable intramedullary insert, as well as a novel method for conveniently and reliably providing such excavation for acceptance of a femoral insert, and especially an upper offset portion of a femoral insert having a configuration and dimensions substantially and/or precisely corresponding to the excavation or aperture made in the femoral neck, all having the foregoing enumerated characteristics and advantages or, in other words, a novel method and device for readying the femoral shaft and neck by providing an excavation therein which is adapted for acceptance of a femoral insert and especially an offset portion thereof.

It is to be understood that the invention is not to be limited to the exact details of construction, operation, or to the exact materials of construction, compositions, methods, procedures, or embodiments shown and described, as obvious modifications and equivalents will be apparent to one skilled in the art, and the invention is therefore to be limited only by the full scope which can be legally accorded the claims appended hereto.

I claim:

1. A rotary reamer device adapted for use in providing an excavation in a femoral superior neck, comprising the following elements in combination:

positioning means adapted to position said rotary reamer device with respect to said femoral neck, cam follower means at a proximal end of said positioning means, rotary reamer means mounted in mounting means for rotation with respect to said femoral neck and adapted for longitudinal and lateral movement with respect to said positioning means by cooperating sleeve and rod means and comprising associated longitudinally-varied camming surface means in said mounting means in moveable contact relationship with said cam follower means, whereby generally lateral movement of said rotary reamer means and its mounting means causes said cam follower means to travel along said camming surface means and said rotary reamer means and its mounting means to seek a longitudinal elevation corresponding to said camming surface means and thereby create in said femoral head a cavity corresponding in longitudinal depth to said camming surface means.

2. A rotary reamer device of claim 1, wherein said rotary reamer means is adapted to be rotatively driven from a rotative power-supply source.

3. A method for excavating the upper end of a femur to provide an excavation therein suitable for the acceptance of an intramedullary insert and an upper flange or offset thereof, which comprises the step of utilizing the device of claim 1.

4. A rotary reamer device adapted for use in providing an excavation in a femoral superior neck, comprising the following elements in combination:

positioning means adapted to position said rotary reamer device with respect to said femoral neck, longitudinal cam follower means associated with said positioning means and at a proximal end thereof, mounting means adapted for longitudinal and lateral movement with respect to said positioning means by intermediate cooperating longitudinally-moveable sleeve and rod means on which said mounting means is slidably mounted, rotary reamer means mounted for rotation with respect to said femoral neck in said mounting means and moveable together therewith, said mounting means comprising longitudinally-varied camming surface means in moveable contact with said longitudinal cam follower means, whereby generally lateral movement of said mounting means and said rotary reamer means mounted therein causes said longitudinal cam follower means to travel along said camming surface means and said rotary reamer means to seek a longitudinal elevation corresponding to said camming surface means and thereby create in said femoral head a cavity corresponding in longitudinal depth to said camming surface means.

5. A rotary reamer device of claim 4, wherein said positioning means comprises shaft means adapted to be inserted in the intramedullary canal of a femur.

6. A rotary reamer device of claim 5, wherein said positioning means comprises an essentially longitudinal member which is capped at a proximal end thereof by said cam follower means.

7. A rotary reamer device of claim 6, wherein said essentially longitudinal member is in slidable relationship with longitudinally moveable sleeve means which is connected to said mounting means and movable longitudinally together therewith.

8. A rotary reamer device of claim 7, wherein said mounting means comprises a distal extension which is apertured for slidable movement therein of essentially lateral rod means extending from said sleeve means and adapted for essentially lateral movement from a distal position to a proximal position with respect to said sleeve means and vice versa.

9. A rotary reamer device of claim 5, wherein said shaft means is flanged or fluted to prevent rotation and is radiused at an upper end to permit close juxtaposition thereof with said reamer means.

10. A rotary reamer device of claim 4, wherein said rotary reamer means is mounted on shaft means which is adapted to be rotatively driven from a rotative power-supply source.

11. A method for excavating the upper end of a femur to provide an excavation therein suitable for the acceptance of an intramedullary insert and a proximal flange or offset thereof, which comprises the step of utilizing the device of claim 4.

12. A method for providing an excavation in a femoral superior neck comprising the steps of 1) providing rotary reamer means mounted in mounting means for longitudinal and lateral movement with respect to positioning means by cooperating sleeve and rod means and associated longitudinally-varied camming surface means in said mounting means and 2) providing positioning means, for positioning said rotary reamer means with respect to said femoral neck, including associated cam follower means at a proximal end thereof movably in contact relationship with said camming surface means, so that generally lateral movement of said rotary reamer means causes said cam follower means to travel along said camming surface means and said rotary reamer means to seek a longitudinal elevation corresponding to said camming surface means and thereby create a cavity in said femoral head corresponding in depth to said camming surface means, and 3) moving said rotary reamer means back and forth generally laterally and thus also longitudinally while maintaining contact engagement between said camming surface means and said cam follower means until completion of said excavation.

13. A method for providing an excavation in a femoral superior neck comprising the steps of 1) providing mounting means which is mounted for longitudinal and lateral movement with respect to positioning means by intermediate cooperating longitudinally-moveable sleeve and rod means on which said mounting means is slidably mounted and rotary reamer means mounted in said mounting means for movement together therewith, said mounting means comprising longitudinally-varied camming surface means and 2) providing positioning means including longitudinal cam follower means at a proximal end thereof movably in contact with said camming surface means, so that generally lateral movement of said mounting means causes said cam follower means to travel along said camming surface means and, due to said cooperating sleeve and rod means, said rotary reamer means to seek a longitudinal elevation corresponding to said camming surface means and thereby create a cavity in said femoral head corresponding in depth to said camming surface means, and 3) moving said mounting means and reamer means mounted therein back and forth generally laterally and thus also longitudinally while maintaining said camming surface means in contact with said cam follower means until completion of said excavation.

14. A method of claim 13, wherein said positioning means comprises shaft means adapted to be inserted in the intramedullary canal of a femur and including the step of so inserting said shaft means.

15. A method of claim 14, wherein said positioning means comprises an essentially longitudinal member which is capped at a proximal end thereof by said cam follower means and including the step of moving said cam follower means along said camming surface means.

16. A method of claim 15, wherein said essentially longitudinal member is in slidable relationship with longitudinally moveable sleeve means which is connected to said mounting means and movable longitudinally together therewith and including the step of moving said sleeve means longitudinally with respect to said longitudinal member.

17. A method of claim 16, wherein said mounting means comprises a distal extension which is apertured for slidable movement therein of essentially lateral rod means extending from said sleeve means and adapted for essentially lateral movement from a distal position to a proximal position with respect to said sleeve means and vice versa and including the steps of moving said distal extension toward and away from said sleeve means.

18. A method of claim 14, wherein said shaft means is flanged or fluted to prevent rotation and is radiused at a proximal end to permit close juxtaposition thereof with said reamer means and including the step of employing said shaft means.

19. A rotary reamer device adapted for use in providing an excavation in a femoral superior neck, comprising the following elements in combination:

positioning means adapted to position said rotary reamer device with respect to said femoral neck, cam follower means at a proximal end of said positioning means, associated longitudinally-varied camming surface means in moveable contact relationship with said cam follower means, rotary reamer means mounted for rotation with respect to said femoral neck and adapted for longitudinal and lateral movement with respect to said positioning means, wherein said rotary reamer means is mounted in mounting means which comprises said camming surface means and which is transversely slidable along rod means affixed to longitudinally-moveable sleeve means on said positioning means, whereby generally lateral movement of said mounting means along said rod means and corresponding movement of said rotary reamer means mounted therein causes said cam follower means to travel along said camming surface means and said mounting means and said rotary reamer means to seek a longitudinal elevation corresponding to said camming surface means and thereby create in said femoral head a cavity corresponding in longitudinal depth to said camming surface means.

* * * * *

UNITED STATES PATENT AND TRADEMARK OFFICE
CERTIFICATE OF CORRECTION

PATENT NO. : 5,468,243
DATED : Nov. 21, 1995
INVENTOR(S) : Alan A. Halpern

It is certified that error appears in the above-indentified patent and that said Letters Patent is hereby corrected as shown below:

Column 3, line 24: "longitudinal-" should read
-- longitudinally- --.

Column 3, line 41: "such a device," should start a new line.

Column 5, line 21: "extends" should read
-- extended --.

Column 5, line 31: Add a -- , --(comma) after the word "retracted".

UNITED STATES PATENT AND TRADEMARK OFFICE
CERTIFICATE OF CORRECTION

PATENT NO. : 5,468,243
DATED : Nov. 21, 1995
INVENTOR(S) : Alan A. Halpern

It is certified that error appears in the above-indentified patent and that said Letters Patent is hereby corrected as shown below:

```
Column 6, line 49 (approx.):  Add a -- , --
      (comma) after the word "extended".

Column 7, line 53:  "longitudinal" should read
      -- longitudinal position --.
```

Signed and Sealed this

Twelfth Day of March, 1996

Attest:

BRUCE LEHMAN

Attesting Officer     Commissioner of Patents and Trademarks